United States Patent
Tsutsumi et al.

(12)
(10) Patent No.: US 6,488,969 B1
(45) Date of Patent: Dec. 3, 2002

(54) METHOD FOR REDUCING BLOOD AMMONIA CONCENTRATION

(75) Inventors: Haruhiko Tsutsumi, Shiki (JP); Takashi Mato, Saitama (JP); Masanori Kamei, Yokohama (JP); Shuichi Hashizume, Yokohama (JP); Ryouichi Ito, Yokohama (JP)

(73) Assignee: Morinaga & Co., Ltd., Tokyo (JP)

( * ) Notice: Subject to any disclaimer, the term of this patent is extended or adjusted under 35 U.S.C. 154(b) by 0 days.

(21) Appl. No.: 10/153,383

(22) Filed: May 22, 2002

Related U.S. Application Data

(62) Division of application No. 09/936,453, filed as application No. PCT/JP00/01635 on Mar. 17, 2000.

(30) Foreign Application Priority Data

| Mar. 17, 1999 | (JP) | ............................................. 11-71594 |
| Feb. 22, 2000 | (JP) | ......................................... 2000-44635 |
| Feb. 22, 2000 | (JP) | ......................................... 2000-44643 |

(51) Int. Cl.⁷ ............................................... A61K 35/78
(52) U.S. Cl. ......................... 424/776; 424/725; 424/439
(58) Field of Search ................................. 424/725, 776, 424/439

(56) References Cited

U.S. PATENT DOCUMENTS 5,728,700 A    3/1998   Heeres et al.

FOREIGN PATENT DOCUMENTS

| JP | 7-274894 | 10/1995 |
| JP | 8-81387 | 3/1996 |
| JP | 8-145991 | 6/1996 |
| JP | 9-249560 | 9/1997 |
| JP | 10-101573 | 4/1998 |
| JP | 10-257869 | 9/1998 |
| JP | 11-1429 | 1/1999 |
| JP | 11-193236 | 7/1999 |
| WO | WO 96/01818 | 1/1996 |
| WO | WO 97/36497 | 10/1997 |

OTHER PUBLICATIONS

Tetsuaki Yamaura et al., "A Device for the Measurement of the Wound Healing and Effects of Solcoseryl® Ointment and Solcoseryl® Jelly", *Applied Pharmacology*, (1981), 565–579, 22 (4).

Katsufumi Sakyo et al., "Effect of Tocoretinate Ointment on Experimental Burn, Open Wound, and Incised Wound in Rat Skin", *Applied Pharmacology*, (1991), 121–137, 42(2).

Shigeru Kamiya, "Inhibition Effect of Tocoretinate Ointment on Pathogenic Bacteria in Digestive Canal", "(Shoku–no kagaku) (Science of foods)", vol. 252, No. 2, pp. 38–45, (Feb. 1999).

*Primary Examiner*—Leon B. Lankford, Jr.
*Assistant Examiner*—Susan D. Coe
(74) *Attorney, Agent, or Firm*—Frishauf, Holtz, Goodman & Chick, P.C.

(57) ABSTRACT

A method for reducing the blood ammonia concentration in a human comprising administering to a human in need thereof a pharmaceutically effective amount of a cocoa component.

5 Claims, No Drawings

METHOD FOR REDUCING BLOOD AMMONIA CONCENTRATION

CROSS REFERENCES TO RELATED APPLICATIONS

This application is a Divisional application of application Ser. No. 09/936,453 filed Sep. 13, 2001 which is a U.S. national phase application under 35 USC 371 of International Application PCT/JP00/01635 filed Mar. 17, 2000.

BACKGROUND OF THE INVENTION

1. Technical Field

The present invention relates to a pharmaceutical, food or drink, and feedstuff, which contain a cocoa component and have an effect for eradicating *Helicobacter pylori*, a wound healing-promoting effect and an effect for reducing blood ammonia concentration.

2. Background Art

*Helicobacter pylori* is a Gram-negative spirillo bacillus separated from gastric mucosa of chronic gastritis patients by Warren and Marshall of Australia in 1983, and it has been reported that this bacillus is separated from gastritis patients and duodenal ulcer patients at high rate.

It has been known that the infection of this bacillus induces acute gastritis and chronic gastritis, and also acts as a recurrence factor and a healing-delay factor of gastroduodenal ulcer. It has been reported by many researchers that the recurrence rate of gastroduodenal ulcer (usually recurred at a rate of 70 to 80% after 1 year) can remarkably be decreased (recurrence rate: 0 to 30%).

Incidentally, the infection rate of *Helicobacter pylori* in Japan increases with age and is as high as about 75% at the age of 40 or higher.

As described above, the elimination of *Helicobacter pylori* has large merit in therapeutics of peptic ulcer, but in reality, the elimination method has been changed with the relation between the merit and side effects.

Firstly, three agents combination therapy using bismuth, tetracycline and metronidazole, recommended in World Society of Digestive System Diseases held in Sydney in 1990, has a merit such that the elimination rate is high (the elimination rate is at least 90%), but it tends to bring about side effects at a high rate and there were many cases that its application can not be continued. After that, in the United States, by the unified view of NIH (National Institute of Health) in 1994, a report was announced that for the *Helicobacter pylori*-positive ulcer patients, therapeutics with an antibacterial agent is needed in addition to therapeutics with an acid secretion inhibitor, irrespective of initiation or recurrence. According to this report, it is firstly reported that the use of a proton pump inhibitor (hereinafter referred to as PPI) as the acid secretion inhibitor and one antibacterial agent in combination is effective and shows less side effect. However, the elimination rate of this method is not necessarily high and can not be said adequate, whereby it has been attempted to change the type of antibacterial agent variously.

It has recently been reported that another one antibacterial agent is further added, namely the use of PPI and two types of antibacterial agents in combination. However, at the present stage, its effectiveness and side effect will be evaluated in the future.

Further, JP-A-11-1429 discloses an anti-*Helicobacter pylori* agent comprising as an active ingredient at least one member selected from peppermint oil, spearmint oil, various types of flavor components and extracts of various natural materials. It also describes in vitro experimental results that an extract obtained from cacao husk or cacao nibs by ethanol extraction shows a growth-inhibiting action against *Helicobacter pylori*.

However, in JP-A-11-1429, with respect to the extract obtained from cacao husk or cacao nibs by ethanol extraction, only in vitro experimental results are indicated, and no effect in clinical tests is confirmed. Further, in Test Example 2 of this publication, results of antibacterial test on humans using limonene and an ethanol extract of cardamon in combination, which shows the highest antibacterial effect, are described. The numerical value of elimination rate of 35% thereby obtained can be evaluated from the viewpoint of no anxiety about side effect, but this elimination rate is so low that its usefulness is considered to be low.

As described in the foregoing, no elimination therapy having both antibacterial effect of 100% against *Helicobacter pylori* and adequate safety, has been established. Accordingly, it is demanded to avoid a multiple agents combination therapy which is complicated and provides large side effect and to establish an elimination therapy which is as simple as possible and provides a high elimination effect and little side effect.

On the other hand, therapies of injuries of surface tissues, i.e. so-called wound, such as surgical incision, gastrointestinal ulcer, burn, laceration or ulcer of skin (e.g. bedsore), are roughly classified into a surgical treatment such as ablation of ulcer tissues, epidermization or suturing, or a conservative treatment mainly made by using an external agent such as an antibiotic agent-containing ointment.

However, these conventional therapies of wound are ones of only awaiting the healing of wound by natural recovery power of organism after all, and therefore a long time is required for recovery and these therapies accompany pains such as soreness.

Accordingly, in order to accelerate the repair and regeneration of tissues at the wound portions positively and directly without relying on the natural recovery power, pharmaceuticals which stimulate or promote steps of differentiation, propagation and the like of cells, have been developed, and frequent use thereof was recently started.

For example, in a local treatment of the conservative treatment, an external agent having actions such as promotion of granulation, improvement of local circulation, or promotion of epidermization, has been used after depuration of wound surface such as protection of the wound surface, removal of slough tissues, or prevention of secondary infection. As such an external agent, an extract from hemolysed blood of young calves (sorcoseryl) (Applied Pharmacology, vol.22, pp 565–579, 1981), tocoretinate (orsenone ointment) (Applied Pharmacology, vol.43, pp 121–127, 1992), and the like have been known. Further, as an internal agent, a decomposition product of lactoferrins (JP-A-8-81387), dehydro epiandrosterone as a steroid hormone secreted from adrenal cortex and its derivatives (JP-A-11-193236), and the like have been proposed.

However, the above agents are not fully satisfactory in all of healing effect, safety, production costs and the like. For example, the above external agents can not be said adequate in the healing effect, the decomposition products of lactoferrins accompany trouble and cost for purification of lactoferrin, and dehydro epiandrosterone has a problem in the safety.

Further, foods that we ingest are degraded to low molecular weight substances such as amino acids and glucose, by the action of digestive enzymes in stomach and small intestine, and absorbed as nutrients in intestinal canal. Residues not digested and absorbed in the intestinal canal are transferred to large intestine, and after moisture content and the like are absorbed, excreted to outside of the body as feces. In large intestine, a lot of enterobacteria exist. Among the enterobacteria, harmful bacteria represented by Welch's bacillus and colibacilli act to degrade and ferment undigested proteins and lipids in the residues, and resultingly produce harmful putrefaction such as ammonia, amine, mercaptan, hydrogen sulfide, indole or scatole, which is a cause of offensive odor of feces (hereinafter referred to as an enteral putrefaction). A part of the enteral putrefaction is absorbed through intestinal wall and enters the blood, but it is usually detoxicated in liver and excreted to outside of the body together with urine by kidney, whereby no serious influence to the human body is caused.

However, it is known that if the putrefaction is stored in the blood by the hypoactivity of liver and kidney, congenital disease (hyperammonemia plasma I and II types, congenital urea cycle enzyme deficiency, and the like) and the like, various adverse effects are caused. For example, it is known that increase of the blood ammonia concentration causes emesis, fever or pyrexia, and in serious cases, hepato celebral encephalopathy.

Accordingly, with persons having the functions of liver or kidney deteriorated or the above congenital disease patients, suppression of the production of entenal putrefaction is important to keep the blood ammonia concentration or the like low.

In the prior art, for the suppression of entenal putrefaction, there have been (1) a method wherein harmful bacteria which produce the putrefaction in intestine are killed by administration of an antibiotic such as neomycin or kanamycin, and (2) a method wherein by using oligosaccharides such as lactulose (bifidus factor) as a supplemental food, useful bacteria such as Lactobacillus bifidus or Lactobacillese is made most dominant is intestine, whereby the propagation of harmful bacteria such as colibacilli and Welch's bacillus is suppressed and as a result, the production of the putrefaction is suppressed.

However, it has also been reported that the method of administering the antibiotic has a possibility of extinguishing not only enteral harmful bacteria but also other useful bacteria, and a defect such that resistant microbe may be developed by frequent uses of the antibiotic, whereby the balance of intestinal bacterium flora may be lost and the reduction of immunological function may be caused.

On the other hand, the above oligosaccharides (bifidus factor) are required to be ingested everyday. However, as the ones to be ingested everyday, most of oligosaccharides are expensive in view of costs.

The present invention has been accomplished in view of such problems of the prior art.

Namely, it is an object of the present invention to provide a pharmaceutical, food or drink, and feedstuff, having an effect for eradicating *Helicobacter pylori*, which provides no side effect and is safe, convenient and excellent in view of nutrition.

It is another object of the present invention to provide a wound healing promoter which has a wound healing effect and is safer and more inexpensive, and a pharmaceutical, food or drink, and feedstuff having a wound healing-promoting effect.

It is further object of the present invention to provide an agent for reducing a blood ammonia concentration which has an effect for reducing the blood ammonia concentration and is safe and more inexpensive, and a pharmaceutical, food or drink, and feedstuff having the effect for reducing the blood ammonia concentration.

SUMMARY OF THE INVENTION

In order to accomplish the above objects, one of the present invention is to provide (A) a pharmaceutical which contains a cocoa component contained in chocolate liquor and has an effect for eradicating *Helicobacter pylori;* (B) food or drink which contains a cocoa component contained in chocolate liquor and other nutrient source, and has an effect for eradicating *Helicobacter pylori;* and (C) feedstuff which contains a cocoa component contained in chocolate liquor and other nutrient source, and has an effect for eradicating *Helicobacter pylori*.

Another one of the present invention is to provide (D) a pharmaceutical which contains a cocoa component contained in chocolate liquor and has a wound healing-promoting effect; (E) food or drink which contains a cocoa component contained in chocolate liquor and other nutrient source, and has a wound healing-promoting effect; and (F) feedstuff which contains a cocoa component contained in chocolate liquor and other nutrient source, and has a wound healing-promoting effect.

Further one of the present invention is to provide (G) a pharmaceutical which contains a cocoa component contained in chocolate liquor and has an effect for reducing a blood ammonia concentration; (H) food or drink which contains a cocoa component contained in chocolate liquor and other nutrient source, and has an effect for reducing a blood ammonia. concentration; and (I) feedstuff which contains a cocoa component contained in chocolate liquor and other nutrient source, and has an effect for reducing a blood ammonia concentration.

With the pharmaceutical of (A), it is preferred to further contain an antibiotic for eradicating *Helicobacter pylori* and/or an acid secretion inhibitor in addition to the cocoa component.

Further, the pharmaceutical, food or drink, and feedstuff may preferably contain cocoa and/or chocolate liquor so as to impart the cocoa component.

Moreover, the food or drink, and feedstuff may preferably contain the cocoa component contained in the chocolate liquor and other nutrient source.

In such a case, as the other nutrient source, a protein, a lipid, a saccharide, a vitamins and a mineral may preferably be contained.

According to the above inventions (A) to (C), by ingesting them, it is expected that an effect for eradicating *Helicobacter pylori* of humans and animals can be obtained, and development and recurrence of acute gastritis, chronic gastritis and gastroduodenal ulcer can be prevented.

According to the above inventions (D) to (F), by ingesting or applying them, it is possible to obtain an effect for promoting wound healing of humans and animals. Here, the "wound" in the present invention includes racoma, laceration, incised wound, braise and the like formed on skin and other tissues (organs), as well as ulcer and burn.

According to the above inventions (G) to (I), by ingesting them, it is expected that an effect for reducing a blood ammonia concentration of humans and animals can be obtained, and symptom of emesis, fever or pyrexia, and hepato celebral encephalopathy by increasing the blood ammonia concentration can be improved.

Further, the pharmaceutical, food or drink, and feedstuff of the present invention contain the cocoa component contained in chocolate liquor as an active ingredient for physiological activity, and therefore it is possible to ingest them safely and conveniently without side effect. Furthermore, since the cocoa component contains dietary fibers and various nutrition components, it is possible to obtain nutrition-feeding effect and health-maintaining effect.

DETAILED DESCRIPTION OF THE INVENTION

In the present invention, the cocoa component means a component of chocolate liquor from which cocoa butter is removed, and mainly contains proteins, saccharides, dietary fibers (water-soluble hardly-digestible polysaccharides, hemicellulose, cellulose, lignin, etc.), phospholipid, inorganic substances (phosphorus, magnesium, calcium, iron, zinc, copper, potassium, sodium, etc.), vitamin A, vitamin B group, vitamin C, vitamin E (various types of tocopherol, etc), niacin, oxalic acid, citric acid, malic acid, succinic acid, lactic acid, acetic acid, tannin (polyphenols such as epicatechin, catechin and quercetin), anhydrous caffeine, theobromine and the like.

In order to impart the above cocoa component, as a material to be added to the pharmaceutical, food or drink, and feedstuff, for example, cocoa powder obtainable by removing cocoa butter from chocolate liquor, or chocolate liquor itself, may preferably be used.

The pharmaceutical of the present invention may be any one so far as it contains the cocoa component as an active ingredient. The form of product thereof is not particularly limited, and may be in various forms such as tablets, powder (granules), capsules and drink. Further, in the case of a pharmaceutical intended to obtain the wound healing-promoting effect, it may be in the form of ointment, medical application and the like.

The food or drink of the present invention may be any one so far as it contains the cocoa component and other nutrient source. The form of product thereof is not particularly limited, and may be produced as cocoa drink, formulated cocoa, chocolate and the like. The other nutrient source is not particularly limited, but proteins such as lactoprotein and soybean protein, lipids such as vegetable oil, saccharides such as sugar and dextrine, vitamins, minerals and the like may preferably be used.

Further, for persons in such a state of pathology that they can not ingest usual meal, for example, persons who have damages of head, face or mouth cavity, consciousness disorder, inappetence or the like, but have normal digestive organs at a certain level, the food or drink of the present invention may be given as an enteral feeding food.

The enteral feeding food may be prepared by mixing the cocoa component and other nutrient source with a nutritional requirement/day as a standard, and used as a powder mixture, or the mixture may be dissolved in water or the like in an adequate amount.

As a method for ingesting the enteral feeding food, for example, for persons who are capable of eating and drinking, it may be ingested orally, or for a persons who are not capable of eating and drinking, a method may be used wherein it is administered through nose using a tube or through an opening formed on stomach or intestine (tube feeding).

Further, the feedstuff of the present invention may be obtained by adding the cocoa component to usual feedstuff.

As the above usual feedstuff, there is no particular limitation, and various feedstuffs commercially available as feedstuff for dog, cat, rat, mouse, hamster, chicken, pig, cow, etc., and ones prepared by appropriately blending ones usually used as feedstuff materials, may be used. Specifically, for example, ones containing protein sources such as soybean lees and white fish meal, lipid sources such as soybean oil, fiber sources such as alphalpha meal, carbohydrate sources such as wheat, corn, wheat bran, germ, yeast, defatted rice bran and milo, vitamins such as vitamins A, $D_3$, E, $B_1$, $B_2$, $B_3$ and $B_{12}$, calcium pantothenate, niacin, folic acid and choline chloride, and minerals such as $CaCo_3$, NaCl, $FeSO_4$, $MnCO_3$ and $CoSO_4.7H_2O$, may preferably be used.

Further, as a method for adding the cocoa component, there is no particular limitation, and the cocoa component may be sprinkled over commercially available feedstuff, blended with other feedstuff materials to form a powder feedstuff, or processed in a pellet-like form.

In the present invention, in the case of the pharmaceutical having the effect for eradicating *Helicobacter pylori,* it is preferred to add an antibiotic for eradicating *Helicobacter pylori* and/or an acid secretion inhibitor. As the antibiotic for eradicating *Helicobacter pylori,* clarithromycin may, for example, be mentioned. Further, as the acid secretion inhibitor, proton pump inhibitor (PPI) and H2 blocker (H2RA) may, for example, be mentioned.

In the present invention, in order to obtain the effect for eradicating *Helicobacter pylori,* it is desirable to ingest the cocoa component in an amount of at least 5 g per day in terms of chocolate liquor.

Further, in order to obtain the effect for eradicating *Helicobacter pylori* by ingesting the cocoa component as the food or drink and feedstuff, it is desirable that the cocoa component is contained in the food or drink and feedstuff in an amount of from 3.5 to 10 wt % in terms of a solid content.

On the other hand, in the present invention, the effective administration amount of the cocoa component to obtain the wound healing-promoting effect, is from 0.8 to 40 g per day in terms of chocolate liquor.

Further, in order to obtain the wound healing-promoting effect by ingesting the cocoa component as the food or drink, it is preferred that the cocoa component is contained in the food of drink in an amount of from 0.1 to 10 mass % in terms of a solid content.

Furthermore, the feedstuff having the wound healing-promoting effect of the present invention, is obtainable by adding the cocoa component to usual feedstuff in an amount of from 1 to 15 mass % in terms of a solid content.

In the present invention, the effective administration (intake) amount of the cocoa component to obtain the effect for reducing a blood ammonia concentration, is from 0.8 to 40 g per day in terms of chocolate liquor.

Further, in order to obtain the effect for reducing a blood ammonia concentration by ingesting the cocoa component as the food or drink, it is preferred that the cocoa component (a component of chocolate liquor from which cocoa butter is removed) is contained in the food or drink in an amount of from 0.1 to 10 mass % in terms of a solid content.

Moreover, the feedstuff having the effect for reducing a blood ammonia concentration is obtainable by adding the cocoa component to usual feedstuff in an amount of from 1 to 15 mass %.

The present invention will be described in detail with reference to examples.

EXAMPLE 1

Formulated Cocoa

Commercially available formulated cocoa (milk cocoa) prepared by blending starting materials of cocoa powder, sugar, dry milk, skim milk and the like in the form of powder, was used as an agent for eradicating *Helicobacter pylori*. The composition in 24 g of this formulated cocoa is as indicated in Table 1, and the calorie thereof was 95 kcal.

TABLE 1

| Proteins | 2.4 g |
|---|---|
| Lipids | 1.8 g |
| Saccharides | 17.2 g |
| Dietary fibers | 1.3 g |

Test Example 1

With patients of gastric ulcer and/or duodenal ulcer, having no history of elimination of *Helicobacter pylori*, the cocoa obtained in the Example was administered while being subjected to a conventional elimination method, to research the elimination effect.

Here, the conventional elimination method is a method wherein a proton pump inhibitor (PPI) as an acid secretion inhibitor and clarithromycin (CAM, 400 mg/day) as an antibiotic for eradicating *Helicobacter pylori* are administered in combination, and then PPI and H2 blocker which is also an acid secretion inhibitor (hereinafter referred to as H2RA) are administered in combination.

Specifically, PPI+CAM administration was carried out for ten days, and subsequently PPI was administered over one month, subsequently H2RA was administered, and then urease method (U), histological test method (P) and culture examination method (C) were carried out for evaluation of elimination. And, if at least two types of inspection i.e. the urease method and the culture examination method, out of these methods, show negative, it can be concluded that the elimination is successful.

Here, the administration of cocoa was carried out by adding about 120 ml of hot water to about 24 g of the commercially available formulated cocoa obtained in Example 1 to obtain one cup amount, and during the above time for elimination, at least one cup was drunk a day. The test results are indicated in Table 2.

TABLE 2

| Patient | Method for elimination | Times of cocoa administration (times/day) | Result | Judge |
|---|---|---|---|---|
| 1 | PPI 6W + (CAM 10 days -> H2RA) | 2 | U: –<br>P: –<br>C: – | o |
| 2 | PPI 8W + (CAM 10 days -> H2RA) | 2 | U: –<br>P: –<br>C: – | o |
| 3 | PPI 6W + (CAM 10 days -> H2RA) | 2 | U: –<br>P: –<br>C: – | o |
| 4 | PPI 8W + (CAM 10 days -> H2RA) | 2 | U: +<br>P: +<br>C: + | x |

From the results of Table 2, it was found that by ingesting the cocoa in combination, it was possible to eliminate *Helicobacter pylori* at a high rate (elimination rate: 75%) as compared with an elimination rate by a conventional elimination method in this facility (45%).

Test Example 2

With patients who had a history of elimination by a conventional elimination method, but were not successful in eradicating, cocoa was administered together with the conventional elimination method as used in Test Example 1, and the elimination effect was researched. The results are indicated in Table 3.

TABLE 3

| Patient | Method for elimination | Times of cocoa administration (times/day) | Result | Judge |
|---|---|---|---|---|
| 1 | PPI 8W + (CAM 10 days -> H2RA) | 2.5 | U: –<br>P: –<br>C: – | o |
| 2 | PPI 8W + (CAM 10 days -> H2RA) | 1.5 | U: –<br>P: –<br>C: – | o |
| 3 | PPI 8W + (CAM 10 days -> H2RA) | 3 | U: +<br>P: –<br>C: – | x |
| 4 | PPI 8W + (CAM 10 days -> H2RA) | 2 | U: –<br>P: +<br>C: – | o |
| 5 | PPI 6W + (CAM 10 days -> H2RA) | 3+ | U: +<br>C: ++ | x |

From the results of Table 3, it was found that by stering the cocoa in combination, 3 out of 5 patients who were not successful in eradicating by the conventional elimination method, were successful in eradicating *Helicobacter pylori*. Further, taking the results of Table 2 together in consideration, by administering the cocoa together with the conventional elimination method, the elimination rate of the conventional elimination method can be improved to a great extent.

Test Example 3

Different from Test Examples 1 and 2, it was attempted to conduct elimination by administering the acid secretion inhibitors (PPI+H2RA) and the cocoa in combination for more than 6 weeks or longer without using the antiseptic for eradicating *Helicobacter pylori*.

The results are indicated in Table 4.

TABLE 4

| Patient | Method for elimination | Times of cocoa administration (times/day) | Result | Judge |
|---|---|---|---|---|
| 1 | PPI 8W + H2RA | 3 | U: –<br>P: –<br>C: – | o |
| 2 | PPI 6W + H2RA | 2 | U: +++<br>P: +<br>C: ++ | x |

As indicated in Table 4, one case out of two cases, was successful. This result shows the possibility of elimination accompanying no substantial side effect.

EXAMPLE 2

Preparation of Feedstuff

A solid feedstuff was prepared (asked Nippon Clea Co.) by adding 12.5% of pure cocoa (tradename: MORINAGA PURE COCOA, manufactured by Morinaga & Co., Ltd.) to feedstuff CE-2 (tradename, manufactured by Nippon Clea Co.). The feedstuff CE-2 contains soybean lees and white fish meal as protein sources, soybean oil as a lipid source, alphalpha meal as a fiber source, wheat, corn, wheat bran, germ, yeast, defatted rice bran and milo as carbohydrate sources, vitamins A, $D_3$, E, $B_1$, $B_2$, $B_3$ and $B_{12}$, calcium pantothenate, niacin, folic acid and choline chloride as vitamins, and $CaCo_3$, NaCl, $FeSO_4$, $MnCO_3$, $CoSO_4 \cdot 7H_2O$ as minerals.

Test Example 4

6 Wister male rats (6 weeks old) preliminarily fed for one week, were separated into two groups (each group consists of 3 rats), and during the test period, CE-2 was freely ingested by a control group, and the cocoa component-containing solid feedstuff obtained in Example 2 was freely ingested by a test group. And, after 2 weeks from the point that the ingestion of the feedstuff started, under anaesthesia of pentobarbital, hairs on the back of each rat was removed and then the skin of about 1 cm square at the hair-removed portion was cut out. Then, the condition of the wound surface was observed everyday (taking a photograph) and the size (area) of the wound surface was measured. The results are indicated in Table 5.

TABLE 5

| | | 3rd day | 7th day | 12th day | Residual rate (%) of wound surface |
|---|---|---|---|---|---|
| Control group | No. 1 | 1.927 | — | — | — |
| | No. 2 | 1.386 | 0.941 | — | 67.9% (7th day/3rd day) |
| | No. 3 | 1.626 | 1.278 | 0.425 | 78.6% (7th day/3rd day) |
| | | | | | 26.2% (12th day/3rd day) |
| | | | | | 33.3% (12th day/7th day) |
| Test group | No. 4 | 1.204 | — | — | — |
| | No. 5 | 0.955 | 0.649 | — | 67.9% (7th day/3rd day) |
| | No. 6 | 1.437 | 0.870 | 0.211 | 60.5% (7th day/3rd day) |
| | | | | | 14.7% (12th day/3rd day) |
| | | | | | 24.2% (12th day/7th day) |

From the results of Table 5, it was found that the size of the wound surface decreased with the lapse of time in both of the control group and the test group. Particularly, in the test group, the residual rate of the wound surface was small and the wound healing was fast.

Further, on the 3rd, 7th and 12th days after the removal of the skin, the tissues of the wound surface including normal portions of the rats of respective groups were collected, and stored in a neutral buffered formalin. And, sections embedded in paraffin of tissues collected by a conventional manner were prepared, and subjected to Azan (modified method) stain ("How to prepare histopathological samples", edited by Yonosuke Watanabe and two others, Igaku Shoin), and then observed by a microscope (100 magnifications). As a result, on the wound surface of the rat (No. 6) of the test group on the 12th day, the epithelial tissue was entirely regenerated and no symptom such as inflammation was seen. However, on the wound surface of the rat (No. 3) of the control group, only a slight regeneration of the epithelial tissue was revealed and a symptom of inflammation was seen.

From the above results, it was found that by ingesting the cocoa component, the wound healing was promoted.

Test Example 5

10 Wister male rats (7 weeks old), were separated into two groups (each group consists of 5 rats), and during the test period, CE-2 was freely ingested by a control group, and the cocoa component-containing solid feedstuff obtained in Example 2 was freely ingested by a test group. And, after 3 weeks from the point that the ingestion of the feedstuff started, feces of rats of respective groups were collected, and odors of feces (ammonia and methylamine) were measured with a Kitagawa type gas detector. Further, with the rats of respective groups, blood was collected from the heart and the ammonia concentration in blood (blood serum) was measured. The results are indicated in Table 6.

TABLE 6

| | | Concentration in feces (ppm) | | Blood ammonia concentration |
|---|---|---|---|---|
| | | Ammonia | Methylamine | ($\mu$g/dl) |
| Control group | No. 1 | 90 | 70.0 | 175 |
| | No. 2 | 21 | 14.4 | 229 |
| | No. 3 | 54 | 44.0 | 319 |
| | No. 4 | 53 | 44.0 | 194 |
| | No. 5 | 8 | 4.0 | 137 |
| | Ave. | 45.20 | 35.28 | 210.80 |
| | SD | 32.07 | 26.32 | 69.01 |
| Test group | No. 6 | 18 | 15.6 | 74 |
| | No. 7 | 14 | 12.0 | 87 |
| | No. 8 | 3 | 3.8 | 158 |
| | No. 9 | 6 | 6.4 | 149 |
| | No. 10 | 3 | 1.6 | 150 |
| | Ave. | 8.80 | 7.88 | 123.60 |
| | SD | 6.83 | 5.81 | 39.77 |

From Table 6, it was found that the average concentrations of ammonia and methylamine in feces of rats of the test group to which the cocoa component was supplied, were remarkably low as compared with the control group. Further, it was also found that the average ammonia concentration in the blood of rats of the test group was low at a level of significance as compared with the control group (risk: 5% or less).

From the above results, it is believed that by ingesting the cocoa component, the formation of ammonia and the like in feces can be suppressed and the blood ammonia concentration can be reduced. Further, although the cause is not known, no definite interrelation between the ammonia concentration in feces and the blood ammonia concentration of each sample was admitted. Accordingly, it is also expected that the absorption of ammonia by intestinal canal might be directly inhibited by the cocoa component.

INDUSTRIAL APPLICABILITY

As mentioned above, according to the present invention, a pharmaceutical, food or drink, and feedstuff having an effect for eradicating *Helicobacter pylori*, a wound healing-promoting effect, and an effect for reducing blood ammonia concentration.

What is claimed is:

1. A method for reducing the blood ammonia concentration in a human comprising administering to a human in need thereof a pharmaceutically effective amount of a cocoa component.

2. The method of claim 1, wherein the cocoa component is orally administered.

3. The method of claim 2, wherein the cocoa component is contained in a chocolate liquor and is administered in an amount of 0.8 to 40 g per day.

4. The method according to claim 2, which further comprises administering with the cocoa component at least one nutrient source selected from the group consisting of a protein, a lipid, a saccharide, a vitamin and a mineral.

5. The method according to claim 3, which further comprises administering with the cocoa component at least one nutrient source selected from the group consisting of a protein, a lipid, a saccharide, a vitamin and a mineral.

* * * * *